US006576451B1

(12) United States Patent
Sumino et al.

(10) Patent No.: US 6,576,451 B1
(45) Date of Patent: Jun. 10, 2003

(54) OLIGOMERS FOR POLYMERIZING TO PRODUCE HYDROUS GELS ENTRAPPING MICROORGANISMS

(75) Inventors: Tatsuo Sumino, Tokyo (JP); Naomichi Mori, Tokyo (JP); Tamio Igarashi, Tokyo (JP); Hiroyoshi Emori, Tokyo (JP); Minoru Kayanoki, Wakayama (JP); Takayuki Nakamura, Wakayama (JP); Ryuichi Matsuyama, Wakayama (JP); Tsutomu Minaki, Wakayama (JP)

(73) Assignees: Hitachi Plant Engineering & Construction Co., Ltd., Tokyo (JP); Shin-Nakamura Chemical Co., Ltd., Wakayama (JP)

( * ) Notice: Subject to any disclaimer, the term of this patent is extended or adjusted under 35 U.S.C. 154(b) by 0 days.

(21) Appl. No.: 09/645,358

(22) Filed: Aug. 25, 2000

(51) Int. Cl.[7] ......................... C12N 11/04; C12N 11/08; C02F 3/00

(52) U.S. Cl. ..................... 435/182; 435/180; 435/262.5

(58) Field of Search ................................ 435/174, 177, 435/178, 180, 182, 262.5

(56) References Cited

U.S. PATENT DOCUMENTS 5,268,397 A 12/1993 Larson ........................ 522/97
5,354,835 A 10/1994 Blair ........................... 528/59

FOREIGN PATENT DOCUMENTS

EP 0 094 222 A1 11/1983
WO WO 93 02971 2/1993

OTHER PUBLICATIONS

Kim et al., "Swelling behavior of novel polyurethane hydro–xerogels", Polymer Bulletin, Jun. 1, 1996, pp 737–744.

Kim et al., "UV–Curable Poly (ethylene glycol)–Based Polyurethane Acrylate Hydrogel", Journal of Polymer Science: Part A Polymer Chemistry, vol. 37, Aug. 1, 1999, pp 2703–2709.

*Primary Examiner*—David M. Naff
(74) *Attorney, Agent, or Firm*—Oliff & Berridge, PLC

(57) ABSTRACT

An oligomer is provided having a polyalkylene glycol main structure, a polymeric double bond group arranged at both ends of the main structure, and a sub-structure arranged between the main structure and each polymeric double bond group. The sub-structures lengthen the main structure, and are composed of a urethane bond and an ethyleneoxy, or a urethane bond, an ethyleneoxy and a propyleneoxy. The introduction of urethane bonds causes crystallization (network formation) with the urethane bonds themselves so that a hydrous gel resulting from polymerizing the oligomer has increased flexibility, strength and erosion resistance. As a result, even though the main structure is lengthened to increase capacity to entrap microorganisms, the strength of the hydrous gel is not reduced. The ethyleneoxy weakens hydrophobicity of urethane regions to improve affinity of the gel for microorganisms. Microorganisms can adhere to and grow on the surface of a hydrous gel produced by polymerizing the oligomer. A hydrous gel containing entrapped microorganisms can be formed by mixing microorganisms with the oligomer and polymerizing. Environmental pollutants can be decomposed using the hydrous gel containing microorganisms.

6 Claims, 5 Drawing Sheets

F I G. 2
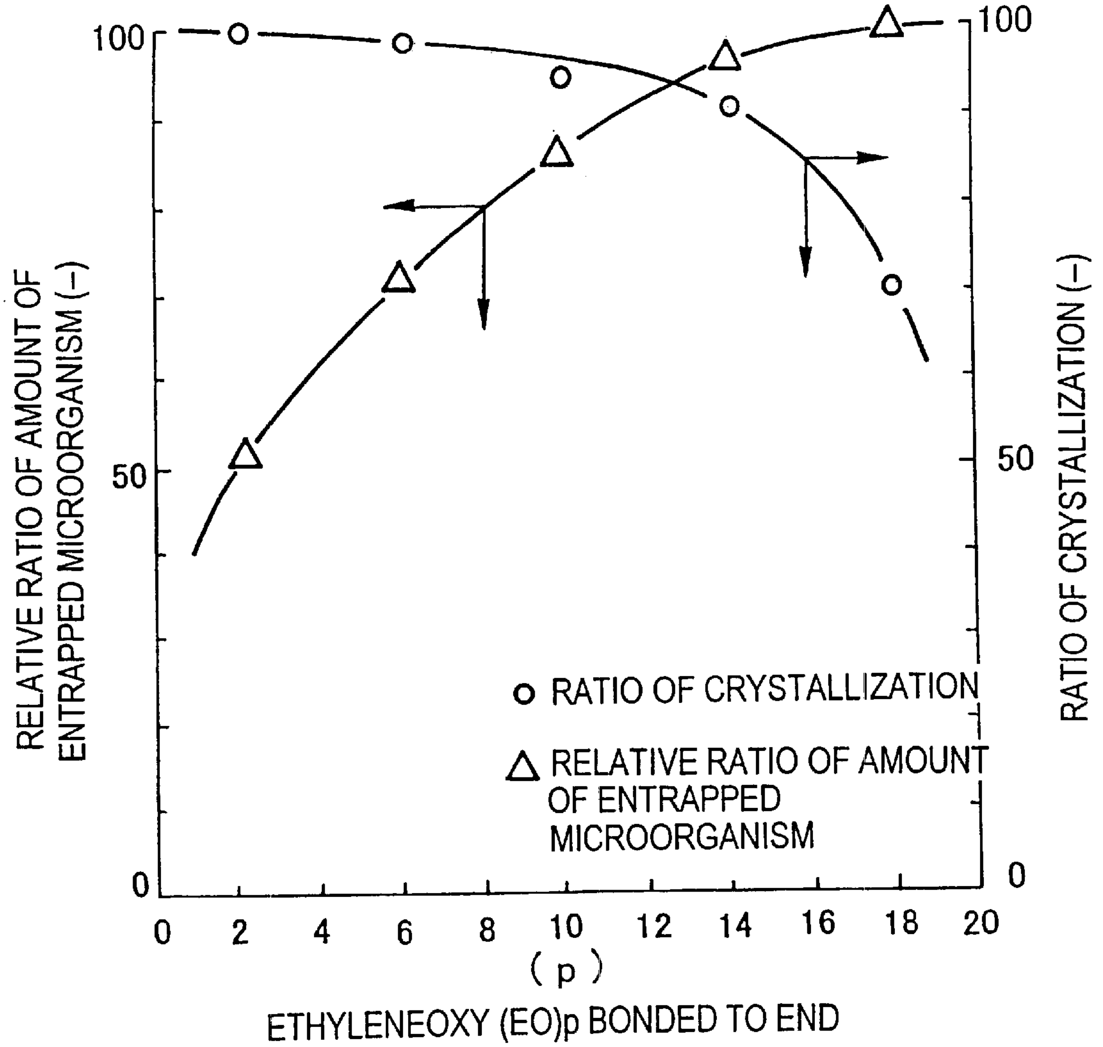

F I G. 3
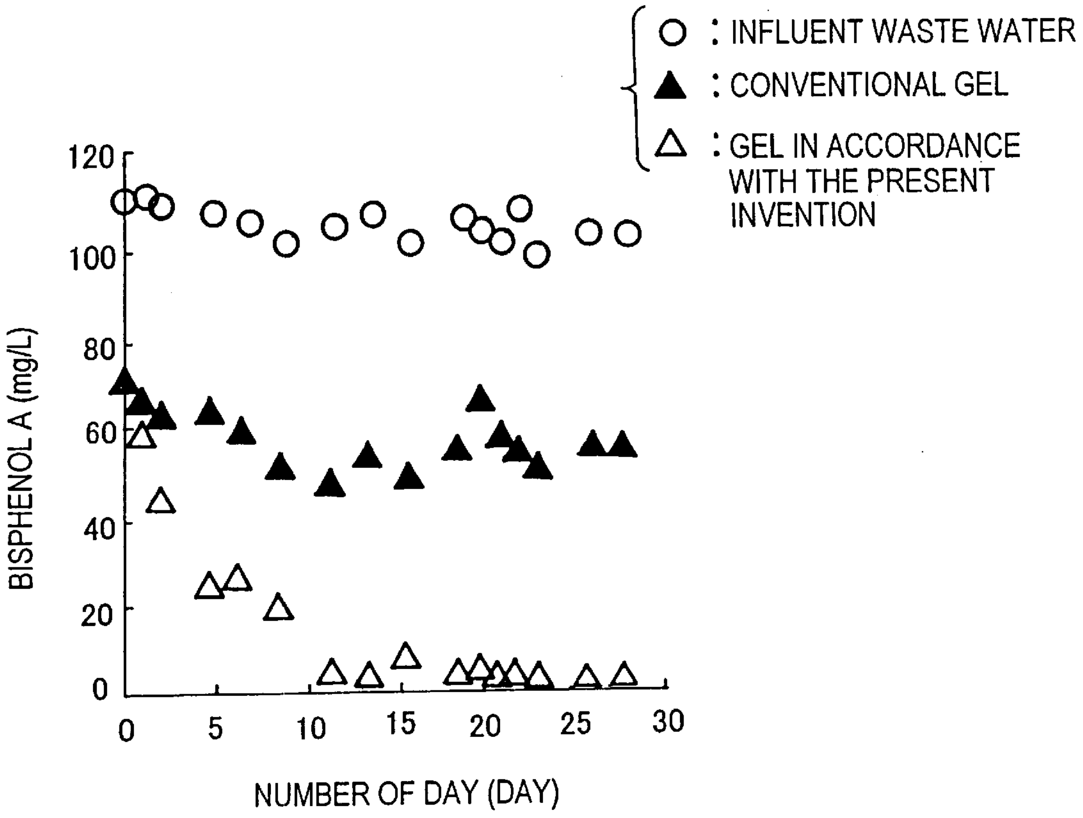
RESULT OF DECOMPOSITION EXPERIMENT OF BISPHENOL A

F I G. 4
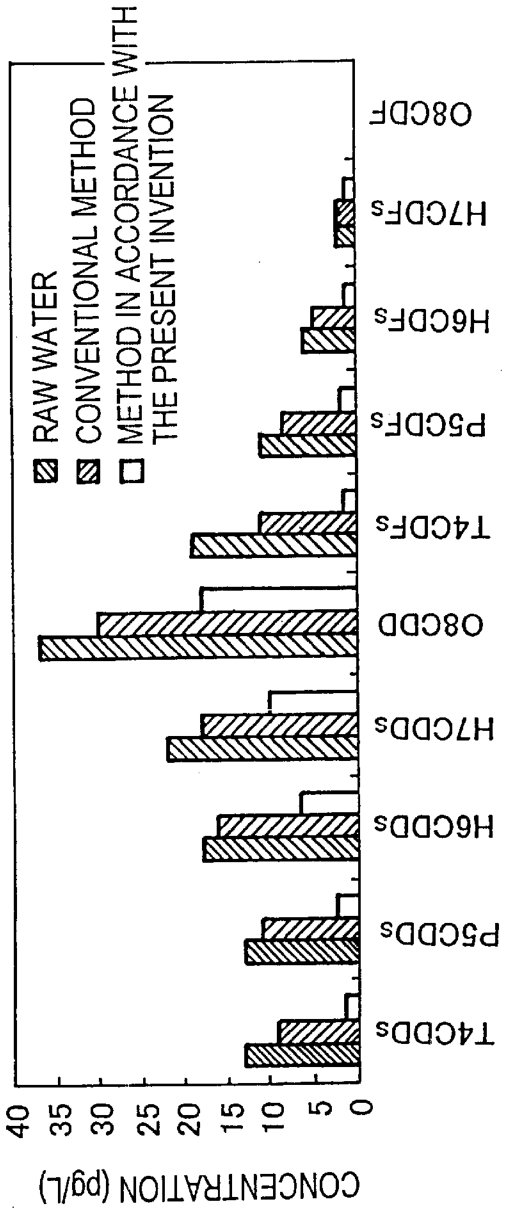
T4CDD : tetrachlorodibenzo-p-dioxin
P5CDD : pentachlorodibenzo-p-dioxin
H6CDD : hexachlorodibenzo-p-dioxin
H7CDD : heptachlorodibenzo-p-dioxin
O8CDD : octachlorodibenzo-p-dioxin
T4CDF : tetrachlorodibenzofuran
T5CDF : pentachlorodibenzofuran
H6CDF : hexachlorodibenzofuran
H7CDF : heptachlorodibenzofuran
O8CDF : octachlorodibenzofuran F I G. 5
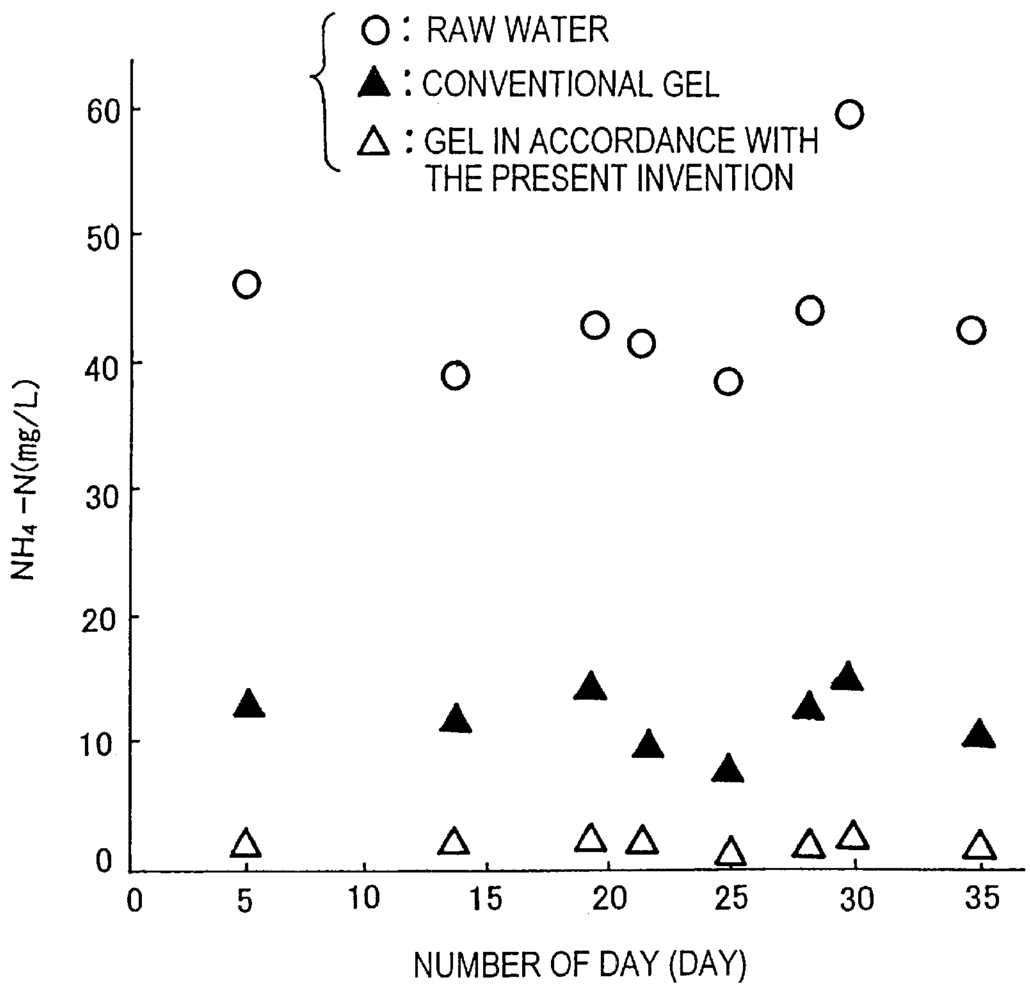

OLIGOMERS FOR POLYMERIZING TO PRODUCE HYDROUS GELS ENTRAPPING MICROORGANISMS

BACKGROUND OF THE INVENTION

1. Field of the Invention

The present invention relates to an oligomer for media to entrap microorganisms, an oligomer-polymerized hydrous gel for the media to entrap the microorganisms, and an oligomer-polymerized hydrous gel entrapping the microorganisms. More particularly, the present invention relates to an oligomer for the media to inclusively entrap the microorganisms, an oligomer-polymerized hydrous gel thereof, and an oligomer-polymerized hydrous gel entrapping the microorganisms in order to biologically treat either inorganic or organic compounds, or to treat both compounds in waste water.

2. Description of the Related Art

Biological treatment of waste water and sewage is widely employed, because the cost thereof is relatively lower than the cost treated chemically or physically. However, certain microorganisms grow slowly, or are easily poisoned. Some microorganisms hardly grow in the environment thereof. Therefore, the biological treatment is not necessarily an efficient one. In order to constructively form the environment in which the microorganisms can easily grow, a treating method in which media adhering the microorganisms on the surfaces thereof are added in waste water, or media inclusively entrapping certain microorganisms are charged in the waste water has already been put into practical use. A gel material entrapping the microorganisms needs to have characteristics to be harmless to the natural environment, not to be degenerated or decomposed by the microorganisms, to be mechanically strengthened, and to have a great capacity to entrap a lot of microorganism. As the gel material already being in practical use, Japanese Patent Application No. 60-44131 discloses a polyethylene glycol oligomer and a polyvinyl alcohol oligomer. The oligomers are polymerized to produce hydrous gel for media to entrap microorganisms. A typical oligomer construction comprises a main structure made of polyethylene glycol and polymeric double bond groups at both ends. The conventional hydrous gel for the media to entrap microorganisms made of polymerized oligomers is superior in entrapping nitrifying bacteria for treating ammonia nitrogen, so that it has been widely utilized.

BRIEF SUMMARY OF THE INVENTION

Object of the Invention

Recently, kinds of environmental pollutants are increased. Biological decomposition of organochlorine substances, endocrine disrupter related substances, dioxins, and the like has been necessary. These substances are decomposed by specific microorganisms. Since a velocity of decomposition by the microorganisms is generally slow, and propagation thereof is slow, it is necessary to maintain a high concentration of the microorganisms in order to increase decomposition efficacy. One of the arts to maintain a high concentration of the microorganisms is an inclusive entrapment art in which the microorganisms are inclusively entrapped in hydrous gel.

However, there is a problem that microorganisms which decompose the endocrine disrupter related substances and the like need the hydrous gel which can entrap a higher concentration of microorganisms than that entrapped in the conventional gel.

SUMMARY OF THE INVENTION

To address the above described problem, an object of the present invention is to provide an oligomer for media to entrap microorganisms, hydrous gel polymerized the oligomers for the media to entrap the microorganisms, and the oligomer-polymerized hydrous gel entrapping the microorganisms, the oligomers having a remarkably greater capacity to entrap a lot of microorganisms, having characteristics not to be degenerated or decomposed by the microorganisms, being mechanically strengthened, and being harmless to the natural environment.

An aspect of the present invention is an oligomer comprising: a main structure made of a polyalkylene glycol; a polymeric double bond group arranged at both ends of the main structure; and a sub-structure, the sub-structure being composed of a urethane bond and an ethyleneoxy, or a urethane bond, an ethyleneoxy and a propyleneoxy, and being arranged between the main structure and the polymeric double bond groups.

According to the above described aspect of the present invention, a main structure is lengthened by inserting the sub-structures composed of urethane bonds and ethyleneoxy or urethane bonds, ethyleneoxy, and propyleneoxy between the main structure made of polyalkylene glycol and the polymeric double bond groups arranged at both ends of the main structure. In addition, the introduction of the urethane bonds causes crystallization (network formation) with the urethane double bonds themselves, so that the hydrous gel becomes flexible and the strength and the erosion resistance thereof are significantly increased. As a result, even though the main structure is lengthened to increase the capacity to entrap a lot of microorganisms, the strength of the hydrous gel does not reduce. Since the hydrophobicity of the urethane regions prevents the inclusive entrapment of the microorganisms, the hydrophobicity is weakened by ethyleneoxy.

Furthermore, hydrophobic alkyleneoxy is introduced between the ethyleneoxy straight structures at a constant ratio as the polyalkylene glycol in the above described aspect of the present invention. Thus, the decomposition of the hydrous gel by the microorganisms can be prevented by the introduction of alkyleneoxy, even though ethyleneoxy having a strong affinity for microorganisms is lengthened to increase a capacity to entrap a lot of microorganisms.

Another aspect of the present invention is an oligomer comprising a following formula, (AA—O)k-B—O(EO)p(PO)q-UA—[O(EO)m(RO)n-UA]e-O(PO-)q(EO)p-B—(O—AA)k, where AA denotes an acryloyl group and a metacryloyl group;

k denotes 1 or 2;

B denotes an alkanepolyol having carbon atoms ranging from 2 to 6 except for a hydroxyl group;

EO denotes $—CH_2—CH_2—O—$;

p denotes an integer ranging from 1 to 15;

PO denotes $—CH_2—CH(CH_3)—O—$;

q denotes an integer ranging from 1 to 14;

UA denotes a group represented by —OCHN—I—NHCO—, wherein —I— denotes an organic diisocyanate except for an isocyanate group;

m denotes an integer ranging from 20 to 100;

e denotes ranging from 1 to 2;

n denotes an integer ranging from 10 to 50; and

R denotes an alkylene group having carbon atoms ranging from 3 to 4.

Furthermore, an example of chemical structures of the oligomers which satisfy the above described conditions according to the above described aspect of the present invention is concretely shown.

Furthermore, an example of the above described chemical structure in which B denotes $—CH_2—CH_2—$ and —I— denotes isophorone group is shown.

Furthermore, the hydrous gel of the polymerized the above described oligomers allows microorganisms to adhere and grow on the surface thereof.

Furthermore, the hydrous gel according to the present invention is polymerized after mixing the oligomers and the microorganisms and can be a medium to inclusively entrap the microorganisms.

BRIEF DESCRIPTION OF THE DRAWINGS

FIG. 2 is a schematic representation of a relationship between the number of ethyleneoxy and a relative ratio of an amount of entrapped microorganisms, and a relationship between the number of ethyleneoxy and a ratio of crystallization, when a sub-structure is composed of a urethane bond and ethyleneoxy;

FIG. 3 is a schematic representation of results of treating waste water containing bisphenol A by media entrapping microorganisms in Example 1 and by media entrapping microorganisms in Comparative example 1;

FIG. 4 is a schematic representation of results of treating waste water containing a variety of dioxins by media entrapping microorganisms in Example 2 and by media entrapping microorganisms in Comparative example 2; and FIG. 5 is a schematic representation of results of treating waste water containing ammonia nitrogen by media entrapping microorganisms in Example 3 and by media entrapping microorganisms in Comparative example 3.

DETAILED DESCRIPTION OF THE PREFERRED EMBODIMENTS

Figure 1:
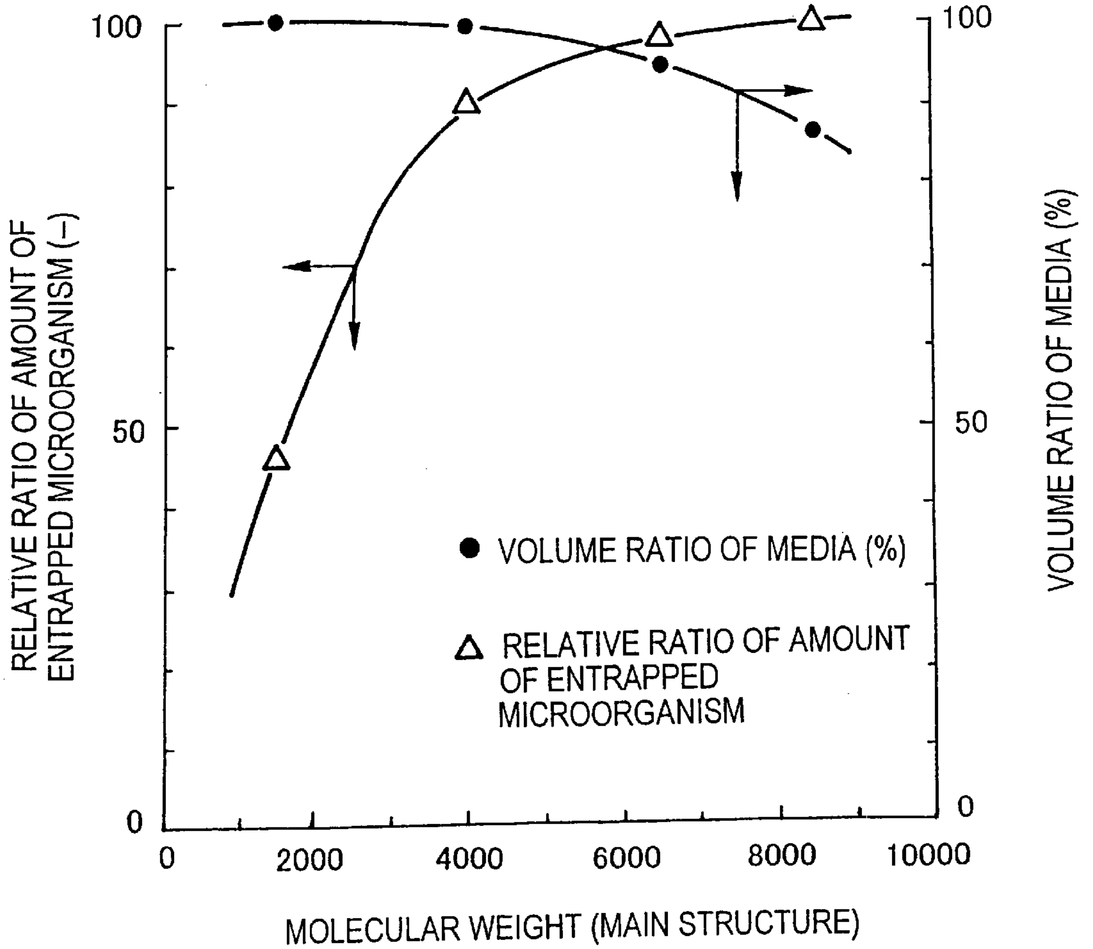
FIG. 1 is a schematic representation of a relationship between a molecular weight of a main structure and a relative ratio of an amount of entrapped microorganisms, and a relationship between the molecular weight of a main structure and a volume ratio of a medium with respect to an oligomer having a structural formula in accordance with the present invention.

Referring to the attached drawings, preferred embodiments of an oligomer for media to entrap microorganisms, oligomer-polymerized hydrous gel for the media to entrap the microorganisms, and the hydrous gel of the polymerized the oligomers entrapping the microorganisms in accordance with the present invention will be described in detail below.

To address a problem that microorganisms which decompose endocrine disrupter related substances and the like need the hydrous gel which can entrap a higher concentration of microorganisms than that entrapped in the conventional gel, the present invention attempts to increase an amount of entrapped microorganisms by enlarging the internal space of the hydrous gel entrapping the microorganism so as to enlarge the size of the microorganisms colonies. With respect to the molecular structures of the oligomers, that is raw material, the following improvements. are performed for this attempt not only to increase the amount of entrapped microorganisms by enlarging the internal space of the hydrous gel but also to satisfactorily have characteristics to be harmless to the natural environment, not to be degenerated or decomposed by the microorganisms, to be mechanically strengthened, the characteristics required as hydrous gel entrapping the microorganisms.

(1) Improvement of the Main Structure of the Oligomers

Ethleneoxy ($—CH_2CH_2—O—$) has been a main structure of polyalkylene glycol which forms a main structure of the conventional oligomers having a molecular weight ranging from 800 to 1200. The above mentioned main structure is lengthened to have a molecular weight which is several times greater than the conventional structure so as to form hydrous gel having larger internal space. In this case, if a main structure made of ethyleneoxy having a strong affinity to the. microorganisms is lengthened, the hydrous gel easily deteriorates due to the microorganisms. As a solution to prevent the decomposition of the ethyleneoxy, the inventors of the present invention have found that combination of hydrophobic alkyleneoxy at a constant ratio can prevent the decomposition of the hydrous gel due to the microorganisms in order to prevent the decomposition of the ethyleneoxy so that the main structure is strengthened, even though the main structure is lengthened. That is, polyalkylene glycol which forms a main structure is preferably composed of block copolymers or random copolymers formed by ethyleneoxy and hydrophobic alkyleneoxy having three carbon atoms (propyleneoxy) or four carbon atoms (butyleneoxy, tetrahydrofuran) rather than ethyleneoxy alone.

(2) Improvement of the Ends of the Oligomers

The improvement of the ends of the oligomers is performed by arranging sub-structures composed of a urethane bond and ethyleneoxy ($—CH_2CH_2—O—$)p, or a urethane bond, ethyleneoxy, and propyleneoxy ($—CH_2—CH(CH_3)—O—$) between the main structure and the polymeric double bond groups. That is, the insertion of the urethane bonds between the main structure and the polymeric double bond groups can crystallize (network formation) with the urethane double bonds themselves after the formation of the hydrous gel by polymerization, so that the hydrous gel can be flexible and the strength and the erosion resistance thereof can be significantly increased. However, the hydrophobicity of the urethane regions remarkably acts by simply arranging the urethane bonds between the main structure and the polymeric double bond groups. Thus, there is a problem that when the microorganisms are intended to adhere or to be entrapped to the oligomers, the oligomers and the microorganisms separate, so that the adhesion or inclusive entrapment is impossible. To address this problem, the inventors of the present invention insert an appropriate amount of hydrophilic ethyleneoxy alone, or ethyleneoxy and propyleneoxy between the urethane bonds and the polymeric double bond groups. In this case, a compounding ratio of propyleneoxy is required to be smaller than that of ethyleneoxy. Thus, an affinity to the microorganisms can increase in spite of the urethane bonds between the main structure and the polymeric double bond groups, so that a hydrous gel which has not only flexibility, strength, and erosion resistance but also a great capacity to adhere and/or entrap a lot of microorganisms can be obtained.

Examples of a urethane crosslinking agent which forms urethane bonds are organic isocyanate groups such as tolylene diisocyanate, 4,4'-diphenylmethane diisocyanate, naphthylene diisocyanate, hydrogenated 4,4'-diphenylmethane diisocyanate, trimethyl hexamethylene diisocyanate, hexamethylene diisocyanate, m-xylylene diisocyanate, tetramethyl xylylene diisocyanate, isophorone diisocyanate, norbornane diisocyanate. These may be used alone or used in combination with not less than two agents.

As described above, an oligomer for media to entrap microorganisms in accordance with the present invention is obtained by improvements of the main structure and ends thereof. The oligomer includes a main structure composed of a polyalkylene glycol; polymeric double bond groups arranged at both ends of the main structure; and sub-structures composed of urethane bonds and ethyleneoxy, or urethane bonds, ethyleneoxy, and propyleneoxy, which are arranged between the main structure and the polymeric double bond groups. In this case, the polyalkylene glycol is preferably the ethyleneoxy (EO)m and alkyleneoxy (RO)n having three or four carbon atoms, m denotes an integer ranging from 20 to 100, and n denotes an integer ranging from 10 to 50. The polymeric double bond groups are preferably acrylate or methacrylate.

As shown in the following formula (1), one example of the improved concrete formula of the main structure and ends of the above described oligomers includes, (AA—O)k-B—O(EO)p(PO)q-UA—[O(EO)m(RO)n-UA]e-O(PO)q(EO)p-B—(O—AA)k (1)

wherein

AA denotes an acryloyl group and a metacryloyl group;

k denotes 1 or 2;

B denotes an alkanepolyol having carbon atoms ranging from two to six except for hydroxyl group;

EO denotes $—CH_2—CH_2—O—$;

p denotes an integer ranging from 1 to 15;

PO denotes $—CH_2—CH(CH_3)—O—$;

q denotes an integer ranging from 1 to 14;

UA denotes a group represented by —OCHN—I—NHCO—, wherein —I— denotes an organic diisocyanate except for isocyanate group;

m denotes an integer ranging from 20 to 100;

e denotes ranging from 1 to 2;

n denotes an integer ranging from 10 to 50; and

R denotes an alkylene group having carbon atoms ranging from 3 to 4.

In the formula (1), B is preferably $—CH_2—CH_2—$, and simultaneously —I— is preferably isophorone group.

An oligomer-polymerized hydrous gel to adhere or to inclusively entrap the microorganisms (hereafter referred to as a medium) is formed by polymerizing the oligomers having the above described construction with a radical reaction added with a polymerization accelerator, a polymerization initiator, a polymerization retarder, and the like. The hydrous gel of the polymerized the oligomers which inclusively entraps the microorganisms (hereafter referred to as a medium entrapping microorganisms) is obtained by suspending microorganisms or activated sludge in an oligomer aqueous solution at a concentration ranging from 5 to 70% to polymerize the oligomers with the radical reaction added with the polymerization accelerator, the polymerization initiator, the polymerization retarder, and the like. A known method can be utilized as a polymerization method of the oligomers.

As described above, the media entrapping microorganisms can be obtained by improving the main structure and the ends which are materials for inclusive entrapment of microorganisms. The obtained medium has a high concentration of the microorganisms through accumulation, is not degenerated or decomposed by the microorganisms, has superior strength and the erosion resistance than the conventional medium, and is harmless to the natural environment. In addition, this oligomer structure is highly permeable to ammonia, trichlene, and dioxins; oxides thereof; gases generated by the metabolism thereof; oxygen; and the like, so that it is preferable as a gel material for a medium entrapping microorganisms utilized for treating waste water.

Gel materials in which concentrations of a polymerization retarder, a polymerization terminator, and a polymerization inhibitor are not more than 300 mg/L, preferably ranging from 50 to 200 mg/L in the oligomers are used for inclusive entrapment of the microorganisms or the active sludge, so that a medium entrapping microorganisms with superior strength and activity is obtained.

Examples of the polymerization terminator, the polymerization inhibitor, and the polymerization retarder will be shown below. These may be used alone or used in combination with not less than two agents.

Examples are quinone polymerization inhibitors such as hydroquinone, hydroquinone monomethylether, p-benzoquinone, methyl-p-benzoquinone, methylhydroquinone, and tert-butyl hydroquinone; amine compounds such as phenothiazine and N,N'-di-2-naphthyl-p-phenylenediamine; phenolic compounds such as 2,6-di-tert-butyl-4-methylphenol and 2,2'-methylenebis(4-methyl-6-tert-butyl phenol); and phosphorous compounds such as triphenyl phosphate and trisnonylphenyl phosphate.

FIG. 1 shows a relationship between a molecular weight of a main structure (—(EO)m(RO)n-) and a relative ratio of an amount of entrapped microorganisms in the case where nitrifying bacteria are inclusively entrapped; and a relationship between a molecular weight of a main structure (—(EO)m(RO)n-) and a volume ratio of a medium which represents decomposition of the medium with respect to the oligomer having the structural formula represented by (AA—O)k-B—O(EO)p(PO)q-UA—[O(EO)m(RO)n-UA]e-O(PO)q(EO)p-B—(O—AA)k in accordance with the present invention.

FIG. 2 shows a relationship between the number of p in ethyleneoxy (EO)p and a relative ratio of an amount of entrapped microorganisms, and a relationship between the number of p and a ratio of crystallization, when a substructure is composed of urethane bonds and ethyleneoxy (EO)p. The ratio of crystallization represents a physical stability of the medium. When a ratio of crystallization is low, there is a problem in that a medium is easily abrasive or the like.

A relative ratio of an amount of entrapped microorganisms [A], a volume ratio of a medium [B], and a ratio of crystallization [C] are represented as following equation. Criteria of denominators for the relative ratio of an amount of entrapped microorganisms are different from each other in FIGS. 1 and 2. In FIG. 1, when the number of microorganisms entrapped with the medium made of a material with a molecular weight of 8400 (the main structure) denoted in the transverse axis is defined to be 100, the number of microorganisms is relatively compared. In FIG. 2, when a number of microorganisms entrapped with the medium made of a material in which p denotes 18 in the transverse axis is defined to be 100, the number of microorganisms is relatively compared.

$$A \text{ in FIG. } 1 = \frac{\text{The number of microorganisms immobilized with the carrier made of a material with each molecular weight}}{\text{The number of microorganisms immobilized with the carrier made of a material with a molecular weight of } 8400} \times 100$$

$$A \text{ in FIG. } 2 = \frac{\text{The number of microorganisms immobilized with the carrier made of a material in which } p \text{ ranges from 2 to 18}}{\text{The number of microorganisms immobilized with the carrier made of a material in which } p \text{ denotes 18}} \times 100$$

$B$ (%)=(A volume of the medium after using for three months/An initial volume of the medium)×100

$C$=(A water content when the medium begins to be sticky/An initial water content of the medium)×100

As shown in FIG. 1, when a molecular weight of polyalkylene glycol which forms a main structure (—(EO)m (RO)n-) increases, a relative ratio of amount of entrapped microorganism significantly increases until a molecular weight of about 4000, then slowly-increases. As shown in FIG. 2, when the number of ethyleneoxy bonded to the ends, which is p in a formula (—(EO)p-), increases, a relative ratio of amount of entrapped microorganism also increases, so that the amount of entrapped microorganism in the media allows increasing.

However, when a molecular weight increases, a volume ratio of medium decreases, so that the media tend to deteriorate (see FIG. 1). When a number of p increases, a ratio of crystallization decreases, so that the media are easily abrasive (see FIG. 2).

As a result, a molecular weight of polyalkylene glycol which forms a main structure ranges preferably from 1500 to 7000. When a sub-structure is composed of urethane bonds and ethyleneoxy (EO)p, the number of p in the ethyleneoxy (—(EO)p-) ranges preferably from 2 to 15. When sub-structures are composed of urethane bonds, ethyleneoxy, and propyleneoxy, that is, when an appropriate amount of propyleneoxy (—(PO)p-) is mixed with ethyleneoxy (—(EO)p-), the decrease in the ratio of crystallization is suppressed, so that the number of p can further increase. In this case, a compounding ratio of propyleneoxy needs to be smaller than that of ethyleneoxy.

Although a volume ratio of medium and a ratio of crystallization are assessed in the case where microorganisms are added and entrapped in FIGS. 1 and 2, the same trend as those seen in FIGS. 1 and 2 is obtained in the case where media without entrapping microorganisms are prepared and assessed.

As a result, media in which a molecular weight of polyalkylene glycol which forms a main structure ranges from 1500 to 7000, and the number of p in the ethyleneoxy ranges from 2 to 15 have a high volume ratio of medium and a high ratio of crystallization, slightly deteriorate, and are less abrasive. Therefore, the medium in accordance with the present invention is utilized not only as a medium to inclusively entrap the microorganism but also as a medium to adhere microorganisms on the surface thereof.

EXAMPLE

Example 1

In this example, bisphenol A which was one of endocrine disrupter related substances was treated using media entrapping microorganisms in accordance with the present invention which inclusively entrapped decomposer of bisphenol A (Sphingomanas sp., $5\times10^6$ cells/mL).

The structure model and a method of producing the oligomers used in Example 1 will be described below.

The structure-model was represented as AA—O(EO)p-UA—O(EO)m(RO)n-UA—(EO)p-O—AA; in which p≈8, m≈54, n≈11, AA denoted metacryloyl, EO denoted ethyleneoxy, PO denoted propyleneoxy, and UA denoted —OCHN—I—NHCO— (in which —I— denoted isophorone diisocyanate except for isocyanate group).

A method of producing this oligomers will be described below. Polyetherpolyol composed of propyleneoxy and ethyleneoxy (trade name: Adekanol 25R-2, Asahi Denka Kogyo K.K.) at an amount of 3100 g (1 mol) and 444 g (2 mol) of isophorone diisocyanate were placed into a 5 L flask equipped with a stirrer, a thermometer, and an air cooling tube, and were stirred. Then, 1.3 g of di-n-butyltindilaurate was added. Although heat of reaction was generated, a reaction temperature was kept ranging from 80 to 90° C. and the synthetic reaction continued for three hours. The reaction solution was cooled to 70° C. with stirring, and 0.44 g (100 ppm) of hydroxynone monomethylether (MEHQ) was added with stirring. Then, polyalkylene glycol monomethacrylate (trade name: Blemmer-PE-350, NOF Corporation) at 868 g (2 mol) was stepwisely added for 30 minutes with stirring. Although heat of reaction was generated, a reaction temperature was kept ranging from 80 to 90° C. and the reaction continued for four hours. Aliquot of the content in the reaction series was taken and subjected to an infrared analyzer (hereafter referred to as IR). Since wavelength corresponding to isocyanate group (2270 $cm^{-1}$) was not detected, the reaction was considered to be completed. The synthesized substance was yellowish solution.

The decomposer of bisphenol A for inclusive entrapment was suspended in the above synthesized 10% oligomer aqueous solution. A polymerization accelerator, a polymerization initiator, a polymerization retarder, and the like were added into this solution for polymerization by a radical reaction, so that media entrapping microorganisms which inclusively entrapped the decomposer of bisphenol A were obtained.

In contrast, the conventional oligomer structure in Comparative example 1 was represented as AA—O(EO)m-AA, in which m denoted 16. A method of inclusive entrapment of the decomposer of bisphenol A was same as Example 1.

With respect to Example 1 and Comparative example 1, the number of microorganisms and compression strength (mechanical strength) after 1-month accumulation in the medium were shown in Table 1.

TABLE 1

| | The number of bacteria entrapped by media | Compression strength |
|---|---|---|
| Example 1 | $8 \times 10^{10}$ cells/mL | 4.0 |
| Comparative Example 1 | $4 \times 10^9$ cells/mL | 3.2 |

As shown in Table 1, the media entrapping microorganisms in Example 1, in which the oligomers in accordance with the present invention were polymerized for inclusive entrapment of the decomposer of bisphenol A, entrapped more microorganisms and had greater compression strength compared with the media entrapping microorganisms in Comparative example 1, in which the conventional oligomers were polymerized for inclusive entrapment of the decomposer of bisphenol A. In addition, the media entrapping microorganisms in Comparative example 1 generated deformation thereof, hydrolysis, and the like due to extended utilization for eight months, so that the compression strength decreased. In contrast, the media entrapping microorganisms in Example 1 did not generate deformation thereof and hydrolysis, so that the compression strength did not decrease.

FIG. 3 shows treatment results, in which waste water containing bisphenol A was treated with the media entrapping microorganisms in Example 1 and the media entrapping microorganisms in Comparative example 1. As a treating condition, a packing ratio of the media entrapping microorganisms in a reaction vessel was set at 10%, and a residence time was set at 18 hours.

In FIG. 3, a mark ○ represented changes over time of the concentrations of bisphenol A in influent waste water, the changes ranging from 100 to 110 mg/L. A mark Δ represented concentrations of bisphenol A in the treated water, when the media entrapping microorganisms in Example 1 were used. A mark □ represented concentrations of bisphenol A in the treated water, when the media entrapping microorganisms in Comparative example 1 were used.

As shown in FIG. 3, the concentrations of bisphenol A in the treated water ranged from 50 to 70 mg/L in Comparative example 1. A remove ratio of bisphenol A was about 50%, which was unsatisfactory.

In contrast, although about ten days were required to stably treat the waste water in Example 1, the concentrations of bisphenol A in the treated water were stably not more than 5 mg/L after the ten-day period, being low level. A remove ratio of bisphenol A was not less than 90%, which was satisfactory.

Example 2

In this example, a variety of dioxins were treated using media entrapping microorganisms in accordance with the present invention which inclusively entrapped decomposer of dioxins (Pseudomonas sp. $5\times10^6$ cells/mL).

The structure model used in Example 2 will be described below.

The structure model was represented as AA—O(EO)p-UA—O(EO)m(RO)n-UA—(EO)p-O—AA, in which p≈6, m≈61, n≈26, AA denoted metacryloyl, EO denoted ethyleneoxy, PO denoted propyleneoxy, and UA denoted —OCHN—I—NHCO— (in which —I— denoted tolylene diisocyanate except for isocyanate group).

The decomposer of dioxins for inclusive entrapment was suspended in the above synthesized 10% oligomer aqueous solution. A polymerization accelerator, a polymerization initiator, a polymerization retarder, and the like were added into this solution for polymerization by a radical reaction, so that media entrapping microorganisms which inclusively entrapped the decomposer of dioxins were obtained.

A method of producing the oligomers was basically same as that in Example 1.

In contrast, the conventional oligomer structure in Comparative example 2 was represented as AA—O(EO)m-AA, in which m denoted 16. A method of inclusive entrapment of the decomposer of dioxins was same as Example 2.

With respect to Example 2 and Comparative example 2, the number of microorganisms and compression strength after 1-month accumulation in the medium were shown in Table 2.

TABLE 2

| | The number of bacteria entrapped by media | Compression strength |
|---|---|---|
| Example 2 | $9\times10^{10}$ cells/mL | 4.5 |
| Comparative Example 2 | $2\times10^{8}$ cells/mL | 3.5 |

As shown in Table 2, the media entrapping microorganisms in Example 2, in which the oligomers in accordance with the present invention were polymerized for inclusive entrapment of the decomposer of dioxins, entrapped more microorganisms and had greater compression strength compared with the media entrapping microorganisms in Comparative example 2, in which the conventional oligomers were polymerized for inclusive entrapment of the decomposer of dioxins. In addition, the media entrapping microorganisms in Comparative example 2 generated deformation thereof, hydrolysis, and the like due to extended utilization for eight months, so that the compression strength decreased. In contrast, the media entrapping microorganisms in Example 2 did not generate deformation thereof and hydrolysis, so that the compression strength did not decrease.

FIG. 4 shows treatment results, in which waste water containing dioxins was treated with the media entrapping microorganisms in Example 2 and the media entrapping microorganisms in Comparative example 2. As treating conditions, a packing ratio of the media entrapping microorganisms in a reaction vessel was set at 10%, and a residence time was set at 24 hours. Ten kinds of dioxins shown in FIG. 4 were examined in this example.

FIG. 4 shows dioxin concentrations in influent waste water, those in treated water using a medium entrapping microorganisms in Comparative example 2, and those in treated water using media entrapping microorganisms in Example 2, each group of bar charts representing the concentrations of the above three kinds of treatment.

As shown in FIG. 4, the concentrations of removed dioxins in the treated water ranged from 10 to 30% compared with those in the influent waste water in Comparative example 2. The remove performance of dioxins was unsatisfactory.

In contrast, the concentrations of dioxins in the treated water in Example 2 were reduced to about 1-half of those in the influent waste water even in the case of dioxins which were hardly removed. The dioxins which were easily removed were reduced to not more than one tenth of those in the influent waste water.

Example 3

In this example, waste water containing ammonia nitrogen was treated using media entrapping microorganisms in accordance with the present invention which inclusively entrapped activated sludge (MLSS: 20000 mg/L) collected from a sewage disposal plant.

The structure model used in Example 3 will be described below.

The structure model was represented as (AA—O)k-B—O(EO)p(PO)q-UA—[O(EO)m(RO)n-UA]e-O(PO)q(EO)p-B—(O—AA)k, in which k≈1, —B— denoted —$CH_2$—$CH_2$—, p≈4, q≈2, m≈70, n≈30, e≈1.2, AA denoted metacryloyl, EO denoted ethyleneoxy, PO denoted propyleneoxy, and UA denoted —OCHN—I—NHCO— (in which —I— denoted tolylene diisocyanate except for isocyanate group).

The activated sludge for inclusive entrapment was suspended in the above synthesized 10% oligomer aqueous solution. A polymerization accelerator and a polymerization initiator were added into this solution for polymerization by a radical reaction, so that media entrapping microorganisms which inclusively entrapped nitrifying bacteria were obtained.

A method of producing the oligomers was basically same as those in Examples 1 and 2.

In contrast, the conventional oligomer structure in Comparative example 3 was represented as AA—O(EO)m-AA, in which m denoted 14. A method of inclusive entrapment of the activated sludge was same as Example 3.

With respect to Example 3 and Comparative example 3, the number of microorganisms and compression strength after 1-month accumulation in the medium were shown in Table 3.

TABLE 3

| | The number of bacteria entrapped by media | Compression strength |
|---|---|---|
| Example 3 | $3 \times 10^{10}$ cells/mL | 5.0 |
| Comparative Example 3 | $2 \times 10^{9}$ cells/mL | 3.8 |

As shown in Table 3, the media inclusively entrapping microorganisms in Example 3, in which the oligomers in accordance with the present invention were polymerized for inclusive entrapment of the activated sludge, entrapped more microorganisms and had greater compression strength compared with the media entrapping microorganisms in Comparative example 3, in which the conventional oligomers were polymerized for inclusive entrapment of the activated sludge. In addition, the media entrapping microorganisms in Comparative example 3 generated deformation thereof, hydrolysis, and the like due to extended utilization for six months, so that the compression strength decreased. In contrast, the media entrapping microorganisms in Example 3 did not generate deformation thereof and hydrolysis, so that the compression strength did not decrease.

FIG. 5 shows treatment results, in which waste water containing ammonia nitrogen was treated with the media entrapping microorganisms in Example 3 and the media entrapping microorganisms in Comparative example 3. As treating conditions, a packing ratio of the media entrapping microorganisms in a reaction vessel was set at 10%, and a residence time was set at 1.2 hours. The temperature of the waste water ranged from 13 to 15° C.

In FIG. 5, a mark ○ represented changes over time of the concentrations of ammonia nitrogen in influent waste water, the changes ranging from 38 to 60 mg/L. A mark Δ represented concentrations of ammonia nitrogen in the treated water, when the media entrapping microorganisms in Example 3 were used. A mark □ represented concentrations of ammonia nitrogen in the treated water, when the media entrapping microorganisms in Comparative example 3 were used.

As shown in FIG. 5, the concentrations of ammonia nitrogen in the treated water were about 10 mg/L in Comparative example 3. In contrast, the concentrations of ammonia nitrogen in the treated water ranged from 1 to 2 mg/L in Example 1, being low level. A stable nitrifying reaction could occur even in the waste water with low temperature.

As described above, an oligomer for a medium to entrap a microorganism, an oligomer-polymerized hydrous gel, and oligomer-polymerized hydrous gel entrapping the microorganism in accordance with the present invention have a remarkably greater capacity to entrap a lot of microorganism, characteristics not to be degenerated or decomposed by the microorganisms, are mechanically strengthened, and are harmless to a natural environment.

Thus, not only ammonia nitrogen but also organochlorine substances, endocrine disrupter related substances, dioxins, and the like can be biologically decomposed with high efficiency.

What is claimed is:

1. An oligomer comprising a following formula, $$(AA—O)_k—B—O(EO)_p(PO)_q—UA—(O(EO)_m(RO)_n—UA)_e—O(PO)_q(EO)_p—B—(O—AA)_k,$$

where

AA denotes an acryloyl group or a metacryloyl group;

k denotes 1 or 2;

B denotes a carbon backbone of an alkanepolyol having carbon atoms ranging from 2 to 6;

EO denotes $—CH_2—CH_2—O—$;

p denotes an integer ranging from 1 to 15;

PO denotes $—CH_2—CH(CH_3)—O—$;

q denotes an integer ranging from 1 to 14;

UA denotes a group represented by —OCHN—I—NHCO—, wherein —I— denotes a carbon backbone of an organic diisocyanate;

m denotes an integer ranging from 20 to 100;

e denotes ranging from 1 to 2;

n denotes an integer ranging from 10 to 50; and

R denotes an alkylene group having carbon atoms ranging from 3 to 4.

2. The oligomer according to claim 1, wherein said B denotes a carbon backbone of an alkanepolyol having 2 carbon atoms and said —I— denotes an isophorone diisocyanate group.

3. An oligomer-polymerized hydrous gel, wherein the polymerized oligomer is one oligomer selected from the group consisting of the oligomers according to claim 1.

4. An oligomer-polymerized hydrous gel, wherein the polymerized oligomer is one oligomer selected from the group consisting of the oligomers according to claim 2.

5. An oligomer-polymerized hydrous gel entrapping a microorganism, wherein the polymerized oligomer is one oligomer selected from the group consisting of the oligomers according to claim 1.

6. An oligomer-polymerized hydrous gel entrapping a microorganism, wherein the polymerized oligomer is one oligomer selected from the group consisting of the oligomers according to claim 2.

* * * * *